United States Patent [19]

Hiratsuka et al.

[11] Patent Number: 5,019,347

[45] Date of Patent: May 28, 1991

[54] INTEGRAL MULTILAYER ANALYTICAL ELEMENT

[75] Inventors: Nobuo Hiratsuka; Asaji Kondo, both of Asaka, Japan

[73] Assignee: Fuji Photo Film Co., Ltd., Kanagawa, Japan

[21] Appl. No.: 481,800

[22] Filed: Feb. 20, 1990

Related U.S. Application Data

[63] Continuation of Ser. No. 227,451, Aug. 2, 1988, abandoned, which is a continuation of Ser. No. 922,760, Oct. 24, 1986, abandoned, which is a continuation of Ser. No. 745,916, Jun. 18, 1985, abandoned.

[30] Foreign Application Priority Data

Jun. 19, 1984 [JP] Japan ................... 59-126267

[51] Int. Cl.⁵ .............................................. G01N 31/22
[52] U.S. Cl. ........................................ 422/56; 422/57; 422/58; 435/805; 436/170
[58] Field of Search ................... 422/56–58; 436/170; 435/805; 210/500.2, 506, 927

[56] References Cited

U.S. PATENT DOCUMENTS

| 127,591 | 12/1887 | Nagatomo et al. | |
|---|---|---|---|
| 3,802,842 | 4/1974 | Lange et al. | 422/57 X |
| 3,992,158 | 11/1976 | Przybylowicz et al. | 422/57 |
| 4,089,747 | 5/1978 | Bruschi et al. | 436/135 X |
| 4,132,528 | 1/1979 | Eikenberry et al. | 436/86 |
| 4,144,306 | 3/1979 | Figueras | 422/56 |
| 4,292,272 | 9/1981 | Kitajima et al. | 422/57 |
| 4,337,222 | 6/1982 | Kitajima et al. | 422/56 |
| 4,435,362 | 3/1984 | Katsuyama et al. | 436/86 X |

FOREIGN PATENT DOCUMENTS

| 0066648 | 12/1982 | European Pat. Off. . |
|---|---|---|
| 0119861 | 9/1984 | European Pat. Off. . |

OTHER PUBLICATIONS

Hiratsuka, et al. Chemical Abstracts, vol. 104, Abstract No. 104:84912a, 1986 (which is based on an EPA published 1/2/86).

*Primary Examiner*—Jill Johnston
*Attorney, Agent, or Firm*—McAulay Fisher Nissen Goldberg & Kiel

[57] ABSTRACT

In an integral multilayer analytical element of a flat sheet type comprising a plurality of layers for quantitative analysis of an analyte in a liquid sample, the improvement which comprises at least two layers of a microporous sheet material arranged adjacent to each other, said at least two layers being combined by an adhesive provided in part on the interface of said layers, whereby the interface allows essentially uniform passage of a liquid therethrough.

7 Claims, 2 Drawing Sheets

(A)　　　(B)　　　(C)

INTEGRAL MULTILAYER ANALYTICAL ELEMENT

BACKGROUND OF THE INVENTION

This is a continuation of application Ser. No. 227,451, filed Aug. 2, 1988, now abandoned which, in turn, is a continuation of application Ser. No. 922,760, filed Oct. 24, 1986, now abandoned, which, in turn is a continuation of application Ser. No. 745,916, filed Jun. 18, 1985, now abandoned.

1. Field of the Invention

This invention relates to an integral multilayer analytical element of a flat sheet type comprising a plurality of layers for quantitative analysis of an analyte in a liquid sample.

2. Description of Prior Arts

As a means for quantitative analysis of an analyte in a liquid sample, an integral multilayer analytical element of a flat sheet type (including flat plate type and flat film type) is known. The integral multilayer analytical element contains a dry analytical reagent, and certain steps of the analytical procedure automatically proceeds within the element. Accordingly, analysis of an analyte in a liquid sample can be easily and quickly performed by applying a liquid sample onto the integral multilayer element. As one representative example of the flat sheet type element, an element of a single layer is known. For instance, an element composed of a single filter paper containing an analytical reagent is disclosed in Japanese Patent Publication No. 36(1961)-4198, and an element composed of a single membrane filter sheet containing an analytical reagent is disclosed in U.S. Pat. No. 3,607,093.

In another example, a non-integral multilayer analytical element comprising separatable layers is known. For instance, there can be mentioned an element using a glass filter or membrane filter as the material of layer disclosed in Japanese Patent Provisional Publication No. 49(1974)-11395 and an element using two filter papers or nets disclosed in Japanese Patent Provisional Publication No. 54(1979)-151096 and U.S. Pat. No. 3,526,480.

Although the above-described element of a single layer type or a separatable layer type is suitable for semi-quantitative analysis, it cannot be reliably employed for quantitative analysis.

Japanese Patent Publication No. 53(1978)-21677 as well as Japanese Patent Provisional Publications No. 55(1980)-164356 and 58(1983)-155100, etc. disclose a flat-type integral multilayer analytical element composed of plural layers with substantially no clearance between the adjoining layers, whereby contemplating assuring the quantitativeness of the analysis. The element comprises a transparent support and a plurality of other layers such as a microporous spreading layer and functional layers which are arranged on one side of the support. The plural layers of the element are constituted in an integral unit and are not separatable.

The microporous spreading layer (hereinafter which may be referred to simply as "spreading layer") is arranged in the outermost position as the top layer to directly receive the applied liquid sample. The spreading layer shows a spreading action on an applied liquid sample. In other words, the spreading layer functions to spread an applied liquid sample therein in such a manner that the liquid sample is distributed in a substantially uniform amount per a unit area, and also is named "metering layer" or "distributing layer". Thus, the spreading layer functions to uniformly supply the applied liquid sample (i.e., supply the liquid sample in such a manner that a substantially equal amount of the sample is distributed per a unit area) immediately to the functional layer positioned next to the spreading layer.

Examples of the functional layers include various layers such as a reagent layer, reaction layer, detection layer, light-shielding layer, light-reflecting layer, filtration layer, semipermeable membrane layer, barrier layer, trap layer, water-absorbing layer, pre-treating layer, migration-inhibition layer, etc. Each layer contains a reagent required in the analysis or is responsible to provide the element with an analytical function. The functional layer and the spreading layer can be designed in one layer-single function type or one layer-multifunction type. For instance, the spreading layer can contain a portion of an analytical reagent to serve further as a reagent layer or can contain a whole analytical reagent to serve further as a reagent layer as well as a reaction layer.

Each of these layers is constituted of a three-dimensional material to form a layer having a certain thickness. The spreading layer is generally made of a structurally microporous sheet such as a membrane filter, particulate-combined matrix, woven fabric, knitted fabric, or filter paper, while the functional layer is generally made of a hydrophilic polymer such as gelatin, polyvinyl alcohol or agar, a cellulose derivative, or a semipermeable material such as poly-dimensional hydrophobic polymer.

In one embodiment of the integral multilayer analytical elements, there is known an element employable for direct analysis of a whole blood. The analysis using the element is performed by applying a whole blood sample directly to the element. FIG. 4 schematically illustrates an elemental structure of the integral multi-layer analytical element for the analysis of whole blood in which the spreading layer is indicated by the numeral 1, and the reagent layer, transparent support and the light-reflecting layer are indicated by the numerals 3, 4 and 7, respectively. In FIG. 4, the symbles L, M, and W indicate a measuring light, a measuring device, and a whole blood sample, respectively. The process involved in the analysis of a whole blood sample using the element of FIG. 4 is as follows. A whole blood sample W is applied in the form of a spot on the spreading layer 1, and the spotted sample spreads therein. The spreading layer 1 traps most of the red blood cells in the whole blood sample, but a small amount of untrapped red blood cells together with a serum reaches the upper surface of the light-reflecting layer 7, as indicated by arrows. The light-reflecting layer 7 is semipermeable and contains a white pigment. The light-reflecting layer filters off the red blood cells completely and shields the color of the blood cell. The liquid sample having passed through the light-reflecting layer penetrates into the reagent layer 3 on the transparent support 1 and reacts therein to form a color. The optical density of thus formed color is then measured by the reflection photometry by means of a measuring light (L) and a measuring device (M).

There is observed, however, a drawback in the above-mentioned integral multilayer analytical element for whole blood analysis. In more detail, the element is not appropriate in the analysis of a lipid or a high molecular weight analyte. The high molecular weight analyte does not pass through the light-reflecting layer 4 in FIG. 4, because the layer 4 is a semipermeable layer. Accordingly, the high molecular weight analyte hardly reaches the reagent layer, and the desired analysis cannot be performed. On the other hand, removal of the light-reflecting layer results in removal of the light-reflecting function to disturb the reflection photometry. In view of the story, it is naturally expected that use of a microporous sheet of allowing passage of high molecular weight analytes can function satisfactorily as the light-reflecting layer. However, until now there is not known an art of tightly combining two microporous sheets (i.e., a microporous spreading layer and a microporous light-reflecting layer) but allowing passage of a liquid sample through the interface between the two sheets. Accordingly, there is not available until now an integral analytical multilayer element using a two porous sheet-combined structure for direct quantitative analysis of a high molecular weight analyte in a whole blood sample.

SUMMARY OF THE INVENTION

The present invention has an object to provide an integral multilayer analytical element of a flat sheet type in which a high molecular weight analyte can pass through a undersurface of a spreading layer and which is employable for analysis directly using a whole blood sample, the analysis being performed by the use of a microporous light-reflecting layer showing a function of shielding a color.

The present invention further has an object to provide an integral multilayer analytical element having a microporous functional layer capable of receiving high molecular weight analytes in addition to a spreading layer and a light-reflecting layer.

The present invention further provides a process for the preparation of the above-mentioned analytical element.

The present invention resides in an integral multilayer analytical element of a flat sheet type comprising a plurality for layers of quantitative analysis of an analyte in a liquid sample, in which the improvement comprising at least two layers of a microporous sheet material arranged adjacent to each other, said at least two layers being combined by an adhesive provided in part on the interface of said layers, whereby the interface allows essentially uniform passage of a liquid therethrough.

In the invention, the essentially uniform passage of a liquid means that a liquid applied on a surface of a microporous layer having continuous micropores is distributed laterally and vertically through the continuous micropores to reach a surface on other side and then the liquid on the latter surface permeates into the adjoining layer without change of the spread area of the liquid.

DETAILED DESCRIPTION OF THE INVENTION

According to the present invention, the two porous sheets should be fixed to each other in part so as to allow the smooth passage of a liquid through the interface thereof. For this purpose, the adhesive should be not be provided throughout on the interface, and is preferably provided on the interface in the form of dots, stripes, a check pattern or islands.

Figure 1:
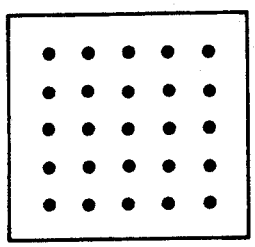
FIG. 1 shows embodiments of patterns of the adhesive on the interface of the layers.
Figure 1:
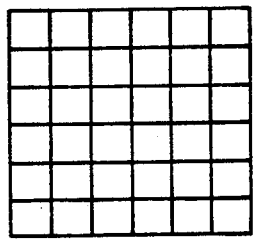
Figure 1:
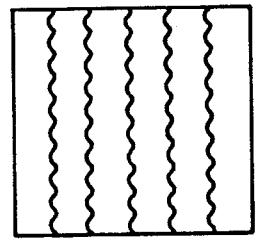

Examples of the pattern of the adhesive are illustrated in FIG. 1.

FIG. 1-(A) shows a pattern of the adhesive in dots arranged regularly in the same manner as the dots used in the printing technology field. The dots can be in the form of circles, squares, stars, or bars. Thus, there is no specific limitation on the shape of dots, and irregularly shaped dots can be employed. Dots which are distributed microscopically at random with variation of shape and/or size of the dots but appear essentially uniformly in total can be employed.

FIG. 1-(B) shows an adhesive in a check pattern.

FIG. 1-(C) shows an adhesive in the form of stripes. There is no specific limitation on the lines constituting the stripes. Straight lines, curved lines, and waved lines can be employed.

The adhesive area ratio, namely, a ratio of the area occupied by the adhesive in the pattern of FIG. 1 (such as dots, lines, etc.) to a unit surface area can be given as in the printing technology field. For this purpose, reference is made to "Textbook of Printing Technology" editted by the Japanese Society of Printing (Gihodo, 1983, page 262 et seq.). In the present invention, the adhesive area ratio is theoretically not higher than 90%, and preferably not higher than 50% and most preferably not higher than 20% from the viewpoint of allowing uniform and smooth passage of a liquid. The size of dots and width of lines of the pattern are so adjusted to be in harmony with the thickness of the microporous sheet to be combined. Generally, the size or width of the pattern is not more than approx. 10 times (preferably not more than approx. 4 times) as much as the thickness of the microporous sheet. Thus, the size and width of the pattern is preferably as small and thin as possible, as far as the desired tight fixation of the microporous sheets is attained. The appropriate space between the dots or lines can be determined experimentally so that no capillary action is produced between the combined two microporous sheets.

For instance, in the case of combining two microporous sheets of a smooth surface such as membrane filters of 150 μm thick, the two microporous sheets can be completely integrated using an adhesive pattern in which the size of dots or width of lines is of approx. 50 to 500 μm, and the space between the adjoining dots or lines is of approx. 0.5 to 3 mm. Thus formed composite structure in which two membrane filters are combined shows the same spreading action on either side. In other words, the upper side or lower side shows almost the same spreading action (i.e., spread area, spread rate, etc.) when receives a liquid sample spotted thereon.

In the case of combining a membrane filter with a plain-woven fabric (cloth) or a knitted fabric, the protruding (or convex) fiber areas of the fabric only can be first provided with an adhesive, and then combined with the membrane filter to give a completely integral composite structure.

Examples of the microporous sheet include a filter paper, nonwoven fabric, membrane filter, woven fabric, knitted fabric (e.g., one in disclosed in Japanese Patent Application No. 59(1984)-79158), fine net, glass filter, particulate-combined sheet, and composited thereof.

A preferred adhesive is a liquid adhesive having a viscosity of not less than 1,000 cps and showing less roping tendency. The liquid adhesive preferably does not permeate into the sheet in the depth direction and remains on the surface of the microporous sheet.

Also employable is a heat-sensitive type adhesive in the form of a string, fiber, and power.

The localized adhesive pattern such as a pattern in dots, strips, check, islands, etc., can be formed by a printing process. For instance, the adhesive pattern can be formed directly on the membrane filter by an intaglio printing. Otherwise, an adhesive pattern is once copied on a release paper and then the copied pattern is transferred on a membrane filter according to an offset process.

Alternatively, a thin adhesive layer is once formed on a tentative support, and such a microporous sheet as a woven fabric or a knitted fabric is pressed thereon. Thus pressed sheet is subsequently removed from the support to obtain a sheet containing adhesive dots on the protruding portions of the fabric. The resulting sheet is then combined with a membrane filter to produce an integral composite structure. In one process, a thin film of an adhesive which is composed of different powdery adhesives and has an appropriate structural viscosity is formed on a tentative support, and a membrane filter is pressed on the support and subsequently is removed therefrom to produce on the filter an adhesive pattern in the form of screenless dots as known in the printing technology.

Otherwise, the screen-printing process using a pattern sheet can be employed. In this process, the adhesive pattern is formed on a microporous sheet directly or via an offset process.

In the use of a non-woven fabric or a glass fiber sheet, the whole portion thereof can be dipped in an adhesive solution, taken out and well squeezed to leave an adhesive only on the surface portion of the fibers. The fabric or sheet having thus produced adhesive pattern is then pressed on a membrane filter, so that the desired portionwise adhesive is attained.

Examples of the functional layers optionally incorporatable into the flat type integral multilayer analytical element of the present invention include a reagent layer, reaction layer, detection layer, light-shielding layer, light-reflecting layer, filtration layer, semipermeable membrane layer, barrier layer, trap layer, water-absorbing layer, pre-treating layer, migration-inhibition layer, and layers having two or more functions.

In the integral multilayer analytical element of the invention, the spreading action is given by one microporous sheet tightly fixed on the adjoining microporous sheet via the portionwise-provided adhesive or by a combination of two more microporous sheets in a composite structure formed by the portionwise-provided adhesive. The composite structure can adequately spread therein an aqueous sample containing microparticles and having a high viscosity such as a whole blood sample.

Concrete examples of the integral multilayer analytical element of the invention which has at least two microporous sheet layers adjoining each other are described below.

Figure 2:
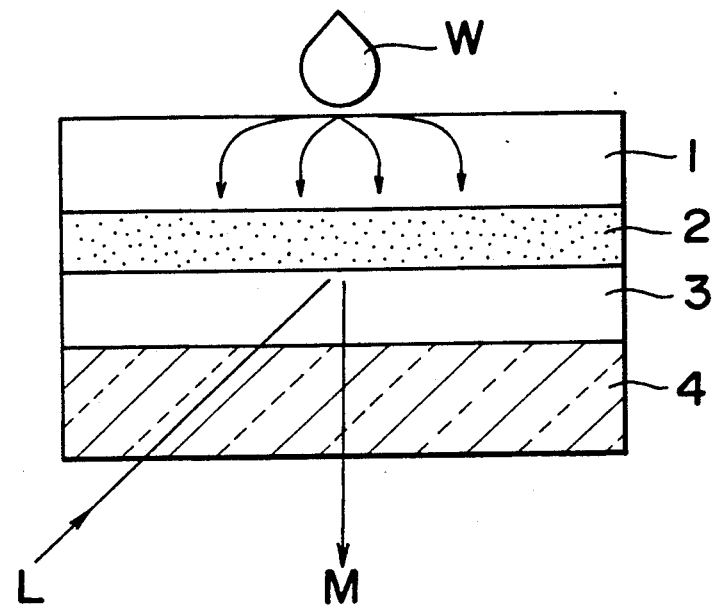
FIGS. 2 and 3 are schematical sections of examples of the integral multilayer analytical elements of the invention.

FIG. 2 shows an integral multilayer analytical element in which a microporous spreading layer 1, a light-reflecting layer 2 and a reagent layer 3 are superposed integrally on a transparent support 4. The spreading layer and the light-reflecting layer both are composed of microporous sheets, and both layers are combined to give an integral structure through a dotted adhesive (one embodiment of the portionwise adhesion).

In the light-reflecting layer, a color-shielding material can be incorporated to shield a color positioned thereon. The light-shielding material generally is a dye or pigment. In the preparation of the light-reflecting layer, a microporous sheet such as a membrane filter can be dyed or charged in the voids with fine powders such as titanium dioxide, barium sulfate, carbon black, carbon microbeads, aluminum microparticulates or microflakes of these material. Moreover, the light-reflecting layers 2 in FIG. 2 can further contain a certain reagent to form a reagent-containing light-reflecting layer. Alternatively, the layer 2 can contain only a reagent in place of the color-shielding material to give a simple reagent layer.

Figure 3:
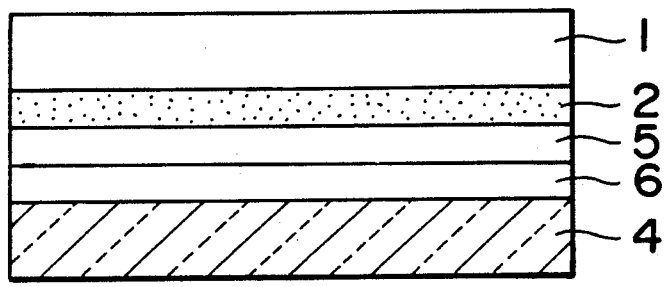
Figure 4:
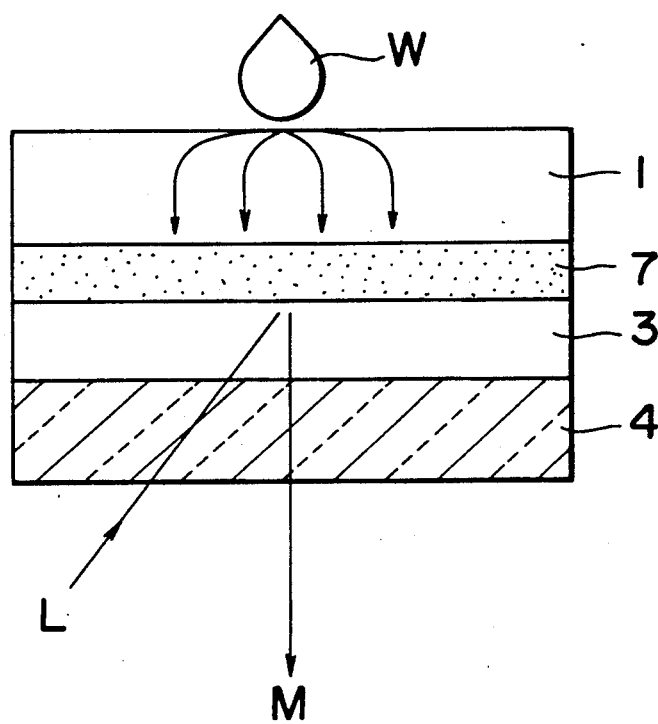
FIG. 4 is a schematical section of a conventional integral multilayer analytical element for analysis using whole blood sample.

FIG. 3 shows one embodiment of the integral multilayer analytical element comprising, from the top, a spreading layer 1, a light-reflecting layer 2, a first reagent layer 5, a second reagent layer 6, and a transparent support 4. In this embodiment, three layers, namely, the spreading layer, the light-reflecting layer and the first reagent layer are made of microporous sheets. The interfaces between the adjoining microporous sheets are fixed to each other through a dotted adhesive (one embodiment of the portionwise adhesion) to give an integral structure. This analytical element is suitable for directly analyzing a high molecular weight analyte such as an enzyme in a whole blood sample.

For performing such analysis, a substrate is incorporated into the first reagent layer and a color-forming reagent is incorporated into the second reagent layer. In the course of analytical operation, an enzyme reacts with the substrate in the first reagent layer to give a low molecular weight product such as hydrogen peroxide or ammonia, which in turn advances into the second reagent layer comprising a color-forming reagent and a gelatin to undergo the desired color-forming reaction. Accordingly, the analytical element having the three microporous sheets is very advantageous if it is used in the analysis of a lipid or high molecular weight analyte. The microporus sheet layer may serve to give a room in which an immunological reation takes place in the case that the analyte is an antigen or antibody of a high molecular weight.

EXAMPLE

Integral Multilayer Analytical Element for Direct Quantitative Analysis of Albumin in Whole Blood Sample An integral multilayer analytical element comprising three microporous sheet layers, a reagent-containing gelatin layer, and a transparent support superposed in this order was prepared as follows.

The following four materials were prepared. (1) A material which was prepared by coating a gelatin layer containing Bromocresol Green Na salt (BCG) on a colorless, transparent polyethylene terephthalate (PET) sheet (thickness 180 μm) to form a dry gelatin layer of 10 μm thick containing BCG in the amount of 0.2 mg. per 1 cm². (2) A microporous sheet material of a cellulose acetate membrane filter (FM-45 available from Fuji Photo Film Co., Ltd., Japan, mean value of maximum pore size 0.45 μm, thickness 40 μm) containing a citrate buffer which had a buffer function to adjust to pH 4.0 when a plasma would be introduced therein. (3) A microporous sheet material of a cellulose acetate membrane filter (pore size 2 μm, thickness 150 μm) containing a titanium dioxide pigment in the amount of 15 g. per 1 m$^2$, which was prepared by a phase inversion process. (4) A microporous sheet material of a polyethylene terephthalate-cotton mix-spinned broad cloth (count 80).

The above-mentioned four materials were combined in the following manner to give an integral structure.

The gelatin surface of the material (1) was wetted with cold water, and immediately it was superposed on the material (2). A silk-screen (pore size 200 μm, space 700 μm) was placed on the material (2), and a starch adhesive was coated thereon through a squeeze method. The screen was subsequently removed to form a dotted adhesive pattern on the material (2). On thus processed material (2) was pressed the material (3) to combine them.

Independently, a vinyl acetate emulsion adhesive (Bond CF 77, tradename available from Konishi Co., Ltd., Japan, solid content 40%, viscosity 50,000-70,000 CP) was coated on a polyester film to form a coated layer of apporox. 30 μm thick. On the coated layer was face-to-face pressed the material (4), and then the material (4) was separated. The material (4) having the portionwise provided adhesive was then pressed on the material (3) of the composite to give a composite structure of the four layers arranged on the transparent PET support.

The composite structure was then dried to give an integral multilayer analytical element for quantitative analysis of albumin.

On the integral multilayer analytical element was spotted a whole blood sample. It was confirmed that the color of the whole blood sample was perfectly shielded from the support side. Further confirmed was that the high molecular weight analyte reached the surface of the gelatin layer.

Based on the above-mentioned findings, whole blood samples having different albumin concentrations were spotted on the integral multilayer analytical element. The albumin concentration and the measured optical density on the blue color given by the albumin-BCG dye were placed on the axis of abscissas and the axis of ordinates, respectively. A satisfactory calibration curve was obtained.

We claim:

1. An integral multilayer analytical element for quantitative analysis having a first microporous sheet and at least one other microporous sheet on a transparent support, said first microporous sheet and other microporous sheet being arranged adjacent to each other to form an interface, wherein said first microporous sheet and other microporous sheet are combined by an adhesive provided in the form of dots, stripes, or a check pattern at the interface so as to allow uniform passage of a liquid through said interface.

2. The intergral multilayer analytical element of claim 1 wherein said other microporous sheet is a microporous light-shielding sheet containing a dye or pigment therein.

3. The integral multilayer analytical element of claim 1 wherein said other microporous sheet is a microporous reagent sheet.

4. The integral multilayer analytical element of claim 1 wherein said other microporous sheet is a membrane filter containing a pigment.

5. The integral multilayer analytical element of claim 1 wherein said adhesive is a liquid adhesive or a heat-sensitive adhesive.

6. The integral multilayer analytical element of claim 1 wherein the ratio of the area occupied by the adhesive to the surface area of said other microporous sheet is not higher than 50%.

7. The integral multilayer analytical element of claim 1 wherein the ratio of the area occupied by the adhesive to the surface area of said other microporous sheet is not higher than 20%.

* * * * *